(12) United States Patent
Brouet et al.

(10) Patent No.: US 11,547,814 B2
(45) Date of Patent: Jan. 10, 2023

(54) DEVICE FOR THE DISPENSING OF A FLUID PRODUCT SYNCHRONISED WITH INHALATION

(71) Applicant: APTAR FRANCE SAS, Le Neubourg (FR)

(72) Inventors: Guillaume Brouet, Rouen (FR); Ludovic Petit, Vitot (FR); David Fabien, Corseul (FR)

(73) Assignee: APTAR FRANCE SAS, Le Neubourg (FR)

( * ) Notice: Subject to any disclaimer, the term of this patent is extended or adjusted under 35 U.S.C. 154(b) by 990 days.

(21) Appl. No.: 16/093,498

(22) PCT Filed: Apr. 13, 2017

(86) PCT No.: PCT/FR2017/050894
§ 371 (c)(1),
(2) Date: Oct. 12, 2018

(87) PCT Pub. No.: WO2017/178767
PCT Pub. Date: Oct. 19, 2017

(65) Prior Publication Data
US 2021/0187210 A1 Jun. 24, 2021

(30) Foreign Application Priority Data
Apr. 15, 2016 (FR) ..................... 1653375

(51) Int. Cl.
*A61M 11/00* (2006.01)
*A61M 15/00* (2006.01)

(52) U.S. Cl.
CPC ........ *A61M 11/007* (2014.02); *A61M 15/008* (2014.02); *A61M 15/0013* (2014.02); *A61M 15/0021* (2014.02); *A61M 2205/3553* (2013.01)

(58) Field of Classification Search
CPC ............ A61M 11/007; A61M 15/0013; A61M 15/0021; A61M 15/008; A61M 2205/3553
See application file for complete search history.

(56) References Cited

U.S. PATENT DOCUMENTS 5,060,643 A * 10/1991 Rich ................. A61M 15/0091
128/200.23
5,347,998 A * 9/1994 Hodson ............. A61M 15/0091
128/200.23

(Continued)

FOREIGN PATENT DOCUMENTS

DE  20 2004 021 188 U1   3/2007
EP    0 441 643 A1       8/1991

(Continued)

OTHER PUBLICATIONS

International Preliminary Examination Report of PCT/FR2017/050894 dated Mar. 23, 2018.

(Continued)

*Primary Examiner* — Timothy A Stanis
(74) *Attorney, Agent, or Firm* — Sughrue Mion, PLLC

(57) ABSTRACT

An inhalation-synchronized fluid dispenser device having a body (10; 10') provided with a mouthpiece (400), a fluid reservoir (100) containing a fluid and a propellant gas being mounted to slide axially in the body (10; 10'), a metering valve (200) including a valve member (210) assembled on the reservoir (100) for selectively dispensing the fluid. The device includes an actuator element (500, 500', 500"; 550) movable and/or deformable between a non-actuation position and an actuation position; an inhalation-controlled trigger system including an inhalation-sensitive member (60, 61; 65, 66) deformable and/or movable under the effect of inhaling and when deformed and/or moved, moving and/or deforming the actuator element (500, 500', 500"; 550) from its non-actuation position towards its actuation (Continued)

position; an electronic dose counter (1000); and a signal-transmitter (1100) for communicating, in particular communicating remotely, information relating to the actuations of the device.

15 Claims, 5 Drawing Sheets

(56) References Cited

U.S. PATENT DOCUMENTS

| | | | |
|---|---|---|---|
| 5,447,151 A | 9/1995 | Bruna et al. | |
| 6,397,839 B1 | 6/2002 | Stradella | |
| 2004/0231667 A1* | 11/2004 | Horton | A61M 15/0065 128/202.13 |
| 2006/0037611 A1* | 2/2006 | Mahon | A61M 15/0091 128/203.15 |
| 2009/0178677 A1* | 7/2009 | Pocock | A61M 15/0075 128/203.15 |
| 2015/0283337 A1* | 10/2015 | Adams | A61M 15/0068 128/202.27 |

FOREIGN PATENT DOCUMENTS

| | | |
|---|---|---|
| FR | 2 775 668 A1 | 9/1999 |
| WO | 92/05824 A1 | 4/1992 |

OTHER PUBLICATIONS

International Search Report for PCT/FR2017/050894 dated Jun. 14, 2017 (PCT/ISA/210).

* cited by examiner

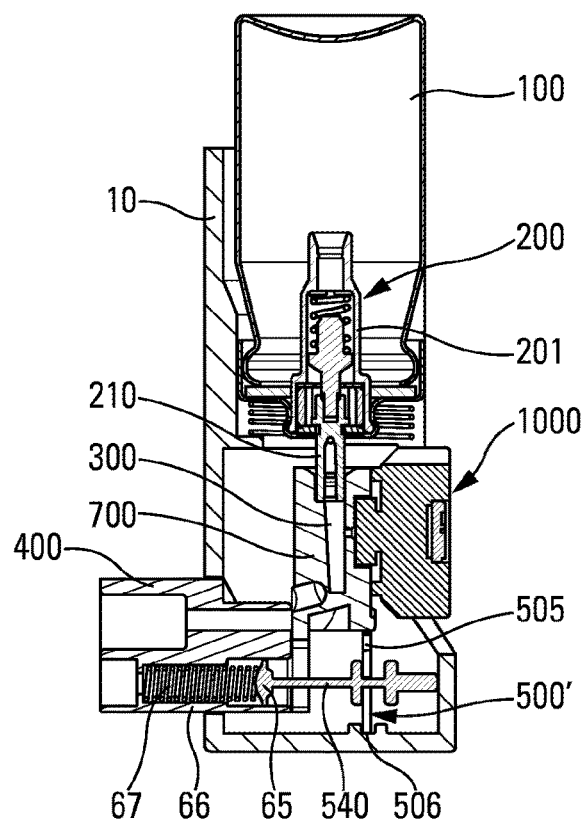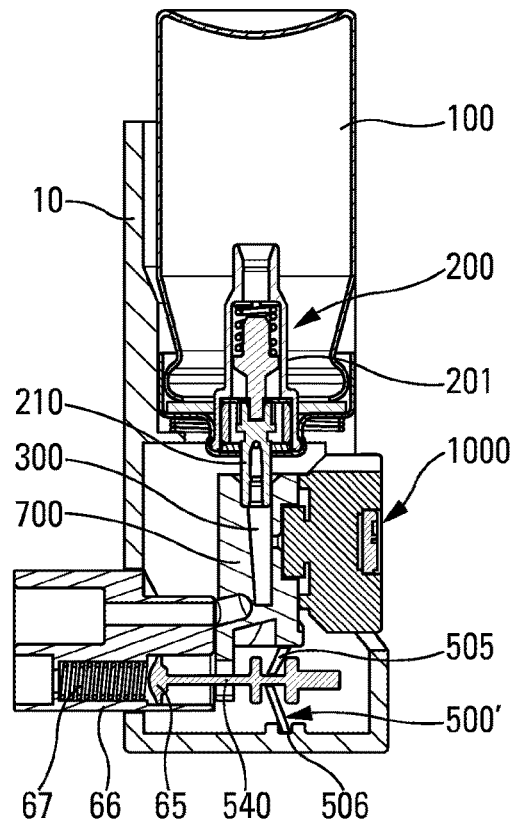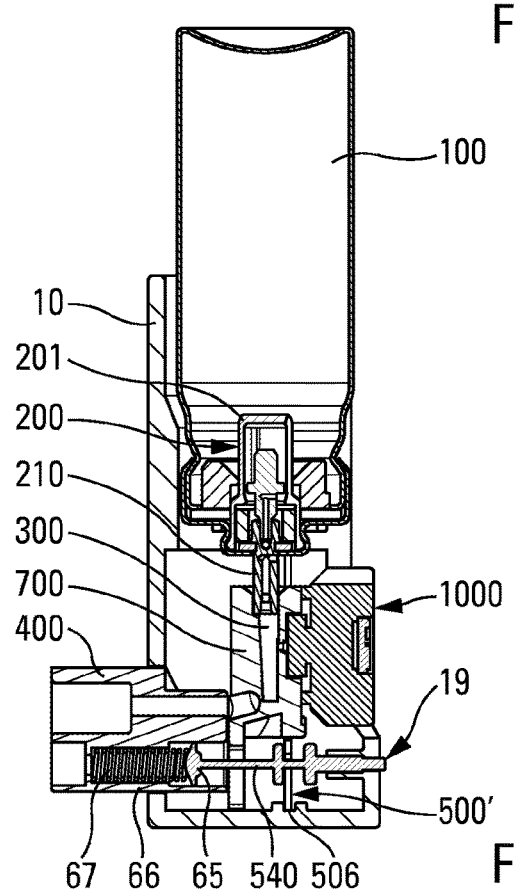

DEVICE FOR THE DISPENSING OF A FLUID PRODUCT SYNCHRONISED WITH INHALATION

CROSS REFERENCE TO RELATED APPLICATIONS

This application is a National Stage of International Application No. PCT/FR2017/050894 filed Apr. 13, 2017, claiming priority based on French Patent Application No. 1653375, filed Apr. 15, 2016.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation. Unfortunately, when the latch releases accidentally, the device is actuated automatically and the dose is dispensed, even when the user does not want it.

Thus, in order to dispense the dose properly, what is more important than actuating the device automatically, is for dispensing to be synchronized with the user inhaling, even if actuation or triggering remains manual.

Document FR 2 775 668 describes a prior-art device.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation.

Another object of the present invention is to provide an inhalation-synchronized fluid dispenser device that minimizes the risks of accidental or unwanted actuation.

Another object of the present invention is to provide an inhalation-synchronized fluid dispenser device that does not present an actuation threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

The present thus provides an inhalation-synchronized fluid dispenser device comprising a body provided with a mouthpiece, a fluid reservoir containing a fluid and a propellant gas being mounted to slide axially in said body, a metering valve including a valve member being assembled on said reservoir for selectively dispensing the fluid, said device further comprising:

an actuator element that is movable and/or deformable between a non-actuation position in which said metering valve cannot be actuated, and an actuation position in which said metering valve can be actuated;

an inhalation-controlled trigger system including an inhalation-sensitive member that is deformable and/or movable under the effect of inhaling, said inhalation-sensitive member, when it is deformed and/or moved, moving and/or deforming said actuator element from its non-actuation position towards its actuation position;

an electronic dose counter; and signal-transmitter means for communicating, in particular communicating remotely, information relating to the actuations of the device.

Advantageously, said actuator element is a blocking element that, in the non-actuation position, co-operates firstly with the body and secondly with the reservoir so as to prevent said reservoir from moving axially in the body.

Advantageously, the device includes a trigger element that is movable and/or deformable between a locking position in which it blocks said blocking element in its blocking position, and a release position in which it does not block said blocking element.

Advantageously, said inhalation-controlled trigger system includes a deformable membrane that defines a deformable air chamber, said deformable membrane being fastened to said trigger element, said deformable membrane being deformed during inhaling, so that it moves said trigger element from its blocking position towards its release position.

Advantageously, said trigger element is accessible manually to the user, so that it can be moved manually towards its release position even in the absence of inhaling.

Advantageously, an actuator member is assembled on the reservoir on the end that is axially remote from said metering valve, said actuator member comprising a hollow sleeve that is axially movable relative to said reservoir between a rest position and a primed position, a spring being arranged between the bottom of the reservoir and the closed top edge of said hollow sleeve, such that when the user presses manually on said actuator member so as to move it towards its primed position, said spring is compressed, so as to transmit an axial force F to said reservoir.

Advantageously, a laterally-actuated pusher is mounted to pivot on the body between a rest position, and a working position in which it axially moves said actuator member into its primed position.

Advantageously, said body includes an opening that connects the mouthpiece to the inside of the body, said opening being closed at the start of inhaling by a check valve, such that the inhalation flow due to inhaling initially passes mainly to the trigger system.

Advantageously, said check valve is opened when said blocking element moves towards its actuation position.

Advantageously, said blocking element comprises an axial extension having a bottom end that is fastened radially and axially relative to said body, and a top end that co-operates with said reservoir in the non-actuation position.

Advantageously, said inhalation-controlled trigger system includes a piston that slides in a chamber between a rest position and an inhaling position.

Advantageously, said blocking element is assembled on a rod that is secured to the piston, so that during inhaling, said rod moves radially, deforming and/or moving said axial extension towards its actuation position.

Advantageously, said actuator element is a locking element that, in its non-actuation position, enables said valve member of the metering valve to move axially in the body, together with said reservoir, preventing said metering valve from being actuated when said reservoir is moved axially in the body without inhaling.

Advantageously, during inhaling, said locking element is moved and/or deformed so that it prevents the valve member from moving axially relative to the body.

Advantageously, said inhalation-controlled trigger system includes a piston that slides in a chamber between a rest position and an inhaling position.

Advantageously, said locking element is secured to a rod that is secured to the piston, so that during inhaling, said rod moves radially, moving said locking element towards its actuation position in which it prevents said valve member of the metering valve from moving axially when said reservoir is moved axially in the body.

These characteristics and advantages and others appear more clearly from the following detailed description, given by way of non-limiting example, and with reference to the accompanying drawings, in which:

FIG. 5 is a diagrammatic section view of a fluid dispenser device, in still another advantageous embodiment, in the rest position;

FIG. 6 is a view similar to the view in FIG. 5, in the dispensing position; and

FIG. 7 is a view similar to the view in FIG. 5, showing a variant embodiment;

Figure 1:
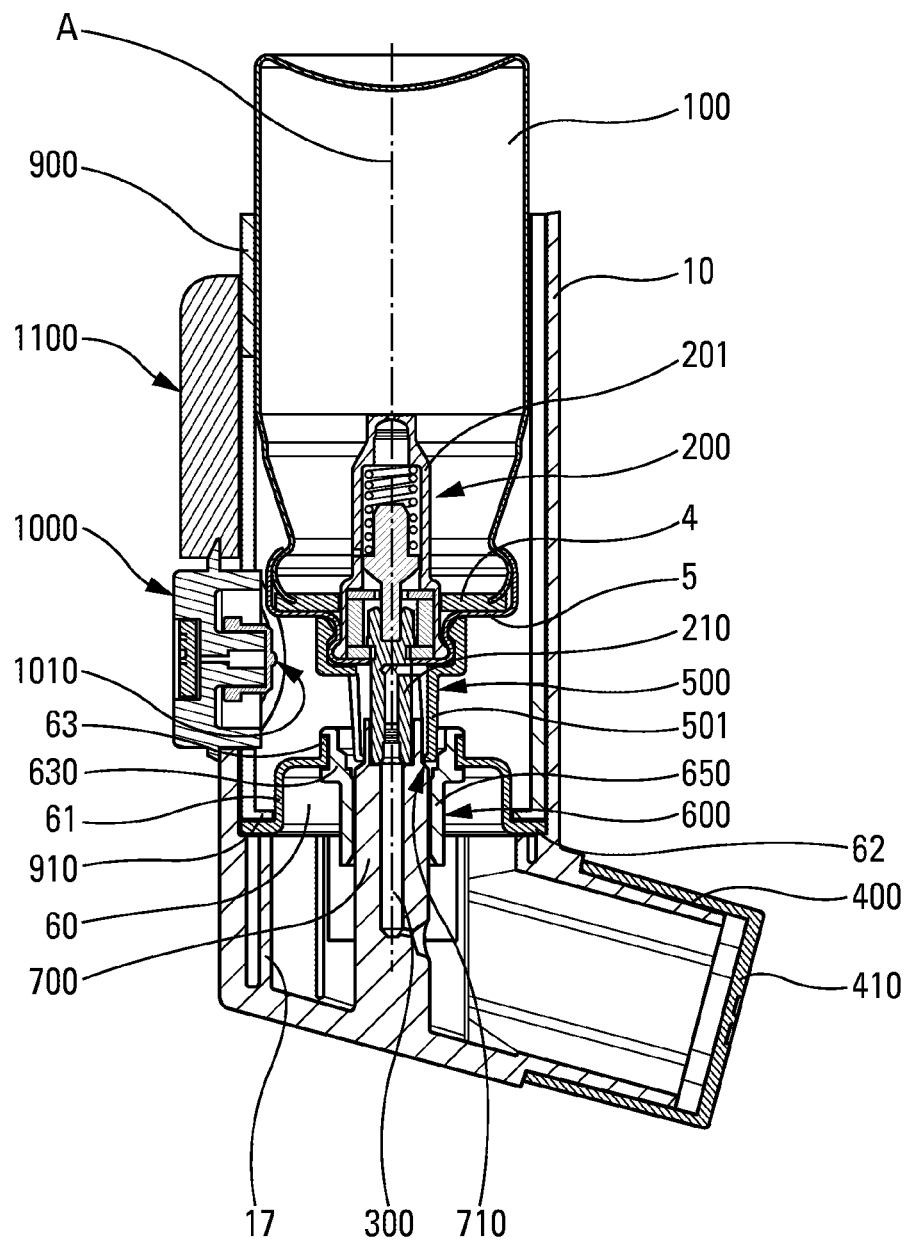
FIG. 1 is a diagrammatic section view of a fluid dispenser device, in a first advantageous embodiment, in the rest position.

In the description, the terms "top", "bottom", "upwards", and "downwards" refer to the upright position of the device shown in particular in FIG. 1. The terms "axial" and "radial" are relative to the vertical central axis A shown in particular in FIG. 1. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show several advantageous embodiments of the invention, but naturally one or more of the component parts described below could be made in some other way, while providing functions that are similar or identical.

With reference to the drawings, the device includes a main body 10 provided with a mouthpiece 400. The mouthpiece 400 defines a dispenser orifice through which the user inhales while the device is being used. The mouthpiece 400 may be made integrally with the body 10, as in FIGS. 1 to 7, or it may be formed on a bottom body portion 10' that is fastened to said main body 10, as in FIGS. 8 to 10. A removable protective cap 410 may be provided on said mouthpiece 400, in particular while it is being stored, that the user removes before use. FIG. 1 shows such a protective cap that could be of any shape.

The main body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body 201, and a valve member 210 that, during actuation, is axially movable relative to said valve body 201, and thus relative to said reservoir 100. The metering valve 200 can be of any appropriate type. It may be fastened to the reservoir 100 via a fastener element, preferably a crimped cap 5, preferably with a neck gasket 4 interposed therebetween.

Advantageously, during actuation, the valve member 210 is stationary relative to the body 10, and it is the reservoir 100 that is moved axially relative to the body 10 between a distal position, which is the rest position, and a proximal position.

The outlet orifice of the valve member 210 of said metering valve 200 is connected via a channel 300 to said mouthpiece 400 through which the user inhales the fluid to be dispensed. In known manner, said valve member 210 is received in a valve well 700 that defines said channel 300, at least in part. In the embodiments in FIGS. 1 and 8 to 10, the valve well 700 is formed integrally with the body 10 or the bottom body portion 10', while in the embodiments in FIGS. 2 to 7, said valve well 700 is axially movable relative to said body 10.

In the invention, the device includes an actuator element 500, 500', 500", 550 that is movable and/or deformable between a non-actuation position in which said metering valve 200 cannot be actuated, and an actuation position in which said metering valve 200 can be actuated. In the rest position, said actuator element 500, 500', 500", 550 is in the non-actuation position, and it is the user inhaling through the mouthpiece 400 that moves and/or deforms said actuator element 500, 500', 500", 550 towards its actuation position. In other words, so long as the user does not inhale, it is impossible to actuate the metering valve 200, and it is only when the user inhales that the metering valve 200 can be actuated, advantageously by pressing manually on the bottom of the reservoir 100.

As described in greater detail below, the actuator element may be a blocking element 500, 500', 500" that, in the non-actuation position, prevents the reservoir 100 from moving axially in the body 10. During inhaling, the blocking element 500, 500', 500" is moved and/or deformed so that it no longer prevents the reservoir 100 from moving axially in the body 10. Thus, after inhaling, such axial movement of the reservoir 100 causes the metering valve 200 to be actuated and a dose of fluid to be dispensed, synchronously with the inhaling.

In a variant, as described with reference to FIGS. 2 to 4, the actuator element may be a locking element 550 that, in its non-actuation position, enables the valve member 210 of the metering valve 200 to move axially in the body 10, together with said reservoir 100, thereby preventing said metering valve 200 from being actuated when said reservoir 100 is moved axially in the body 10 without inhaling. During inhaling, the locking element 550 is moved and/or deformed so that it prevents the valve member 210 from moving axially relative to the body 10. Thus, after inhaling, axial movement of the reservoir 100 causes the metering valve 200 to be actuated and a dose of fluid to be dispensed, synchronously with the inhaling.

Thus, in the various above-described variants, in the absence of inhaling, there is no risk of an active dose of fluid being lost by accidental or incomplete actuation during which the user does not inhale. Actuating the valve 200 and expelling a dose of fluid are thus possible only when the user inhales and simultaneously presses on the reservoir 100 so as to actuate the valve 200.

The device includes a trigger system that is controlled by the user inhaling, and that is for moving and/or deforming said actuator element 500, 500', 500", 550 from its non-actuation position towards its actuation position, when the user inhales through the mouthpiece 400.

The trigger system includes an inhalation-sensitive member 60, 61, 65, 66 that is deformable and/or movable under the effect of inhaling, the inhalation-sensitive member 60, 61, 65, 66 being adapted, when it is deformed and/or moved, to move and/or deform said actuator element 500, 500', 500", 550 from its non-actuation position towards its actuation position.

As described in greater detail below, the inhalation-sensitive member may be made in the form of a deformable membrane 61 that defines an air chamber 60, e.g. a bellows or a deformable pouch.

In a variant, as described with reference to FIGS. 2 to 7, the inhalation-sensitive member may be made in the form of a piston 65 that is preferably cylindrical, and that slides in a chamber 66 that is preferably cylindrical and non-deformable.

In the invention, the device includes electronic modules.

In particular, an electronic dose counter 1000 is provided. In particular, the counter 1000 can detect the movements of the reservoir 100, e.g. by means of a contact sensor 1010. In a variant, the counter 1000 could be connected to a sensor, in particular a membrane sensor, that detects the dose of fluid being dispensed, e.g. in the valve well 700. The electronic counter 1000 may be actuated in other ways, e.g. by detecting the movement of the valve member 210 of the metering valve relative to the valve body 201.

The device also includes signal-transmitter means 1100 for communicating, in particular communicating remotely, information relating to the actuations of the device. In particular, the body 10 may include a signal-transmitter module, for communicating remotely with any base. Appropriate power supply means are advantageously provided.

In particular, the electronic module may advantageously comprise a card that includes an electrical switch that sends a pulse. The module may also comprise a display and/or use a Bluetooth or Wifi connection for sending information to an accompanying peripheral. Appropriate sensors, such as flowrate and/or pressure sensors, may be provided for detecting various parameters of the inhalation flow.

Associated with a dose counter 1000 that counts each dose that is actually dispensed, and with the inhalation-synchronized device of the invention, the signal-transmitter means 1100 make it possible for each dose that has been dispensed to be transmitted in completely reliable manner, e.g. to a doctor or to any other person wishing to monitor the use of the inhaler device by the user. The inhalation-synchronized device guarantees that the user inhales each time the user actuates the device, and the counter records each dose that is dispensed, together with various associated parameters, such as a timestamp for each dispensing and characteristics of the inhalation. In this way, the doctor can know very accurately the conditions of use of the device by the user.

In a first embodiment shown in FIG. 1, the non-actuation position corresponds to a position in which the reservoir 100 is blocked in the body 10. In this blocked position, the reservoir 100 is prevented from moving by said actuator element that is released only at the moment of inhaling.

In this embodiment, the actuator element, forming the blocking element, is advantageously formed by a blocking ring 500 that includes at least one, and preferably three, axial blocking tabs 501 that are elastically deformable radially outwards. The blocking ring 500 is fastened, in particular snap-fastened, on the reservoir 100, in particular on the cap 5 that fastens the metering valve 200 on the reservoir 100. In the rest position, said blocking tabs 501 bear against a radial shoulder 710 of said valve well 700. The shoulder preferably slopes downwards and radially outwards, such that when the reservoir 100 slides axially in the body 10 during actuation, said axial blocking tabs 501 slide over said sloping shoulder 710, thereby deforming them radially outwards.

A trigger element 600 is mounted around said valve well 700 to slide axially between a blocking position in which it blocks said blocking ring 500 in its non-actuation position, and a release position in which it no longer blocks said blocking ring 500. In particular, in the embodiment in FIG. 1, said trigger element 600, in the blocking position, co-operates with said blocking tabs 501, preventing any deformation radially outwards of said blocking tabs 501. Thus, when said trigger element 600 is in the blocking position, it prevents said blocking tabs 501 from deforming radially outwards, which blocking tabs consequently remain blocked axially by said shoulder 710 of the valve well 700, thereby preventing the reservoir 100 from moving axially and the metering valve 200 from thus being actuated. Optionally, slide means, such as balls, could be interposed between the valve well 700 and the trigger element 600, so as to make it easier for said trigger element to slide during inhaling.

The trigger element 600 advantageously comprises a hollow central sleeve 650 that slides axially around the valve well 700. Two axial tabs (not shown) that are diametrically-opposite and that are each connected to said central sleeve 650 may be provided so as to co-operate with a respective opening of the body 10, for substantially closing the openings in the blocking position, and for substantially opening the openings in the release position. Since the openings are closed at the start of inhaling, the inhalation flow due to inhaling initially passes mainly to the trigger system, in this embodiment the deformable air chamber 60. This makes it possible to optimize such triggering by inhaling. When the trigger element 600 is moved axially towards its release position under the effect of inhaling, and thus when the user can actuate the metering valve 200 so as to dispense a dose of fluid, the axial tabs open said openings of the body 10, and this draws in air and thus increases the inhalation flow. This optimizes synchronization between the user inhaling and dispensing the dose, and also promotes good dispensing of the dose into the user's lungs.

Advantageously, said axial tabs may be accessible from the outside through said openings. This makes it possible, if necessary, to move the trigger element 600 manually, so as to be able to actuate the metering valve 200 even without inhaling, e.g. when the person that needs to receive the dose of fluid is incapable of inhaling sufficiently. This is thus a safety measure. In a variant to this safety measure, an axial extension (not shown) could be provided that is secured to the trigger element 600, e.g. extending sideways from the reservoir 100, and accessible to the user from the outside of the body 10.

In a variant, the trigger element 600 need not include axial tabs, and the body need not include the openings 13. In this configuration, the inhalation flow could flow axially in the body 10, around the valve well 700, which could be encouraged by a central sleeve 650 provided with axial cutouts for passing the flow of air.

In the embodiment in FIG. 1, the inhalation-sensitive member is made in the form of a deformable air chamber 60. Advantageously, the air chamber comprises a deformable membrane 61 that is connected firstly to the body 10 and secondly to said trigger element 600. Advantageously, a membrane-carrier sleeve 900 is arranged in stationary manner in the body 10, with a bottom shoulder 910 that jams a first edge 62 of the membrane 61 against a portion 17 of the body 10. The second edge 63 of the membrane 61 may be fastened in a channel 630 of the trigger element 600, advantageously formed in the hollow central sleeve 650 of said trigger element.

Figure 8:
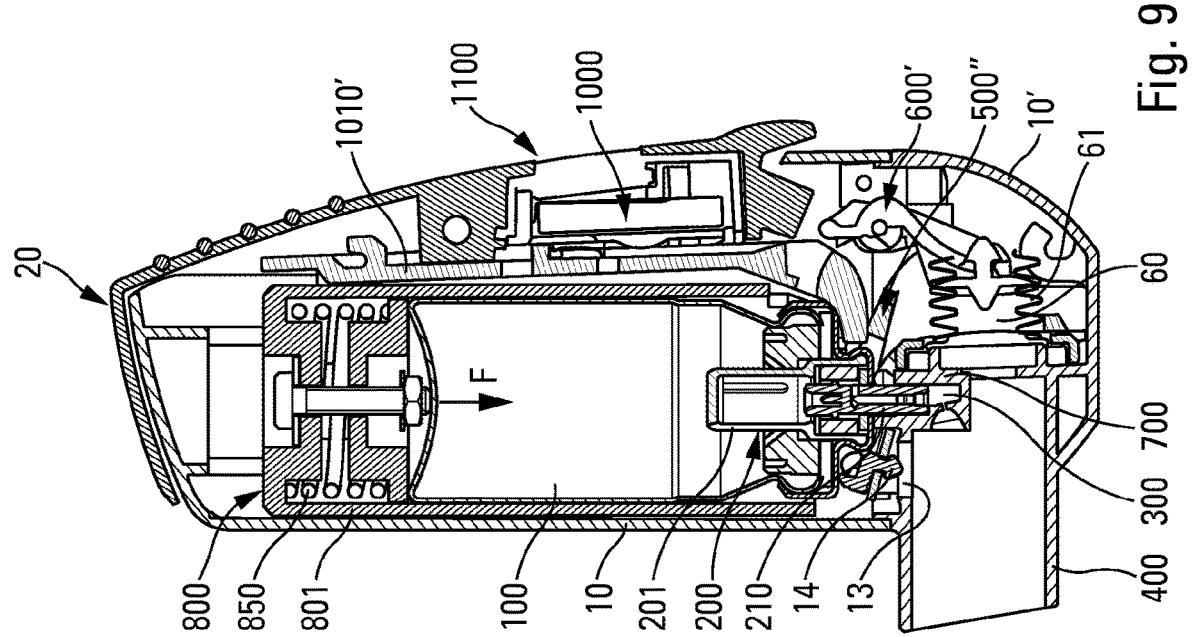
FIG. 8 is a diagrammatic section view of a fluid dispenser device, in still another advantageous embodiment, in the rest position.
Figure 9:
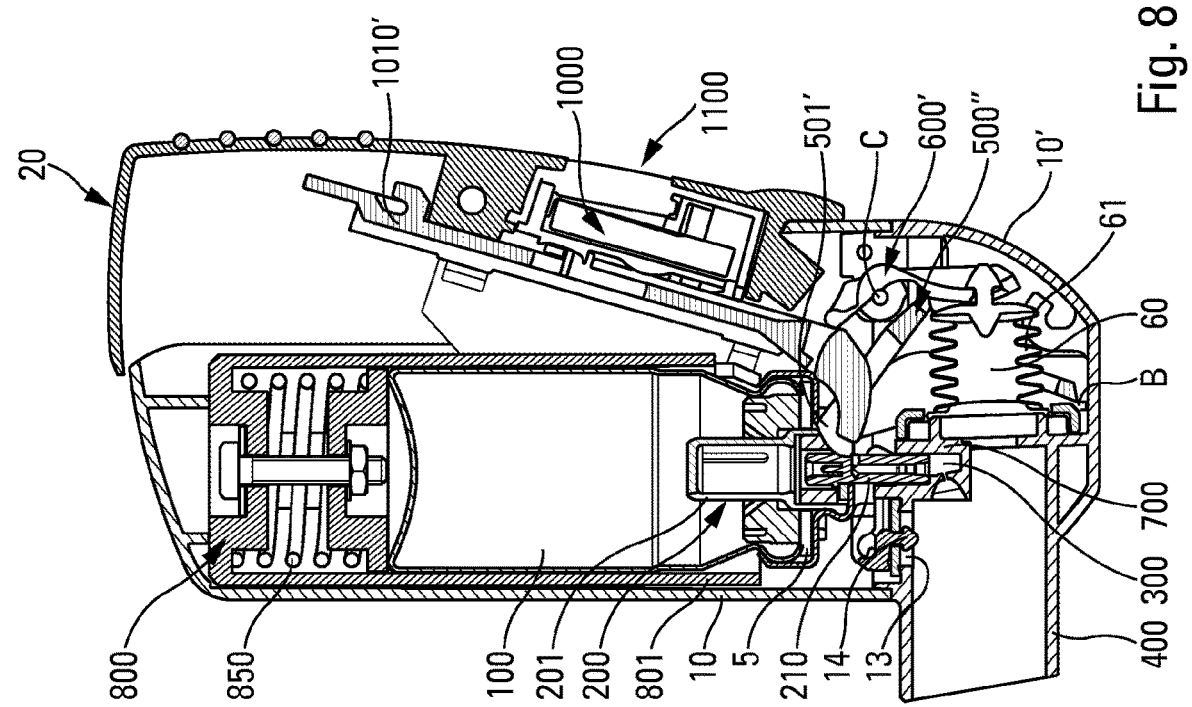
FIG. 9 is a view similar to the view in FIG. 8, shown after inhalation.
Figure 10:
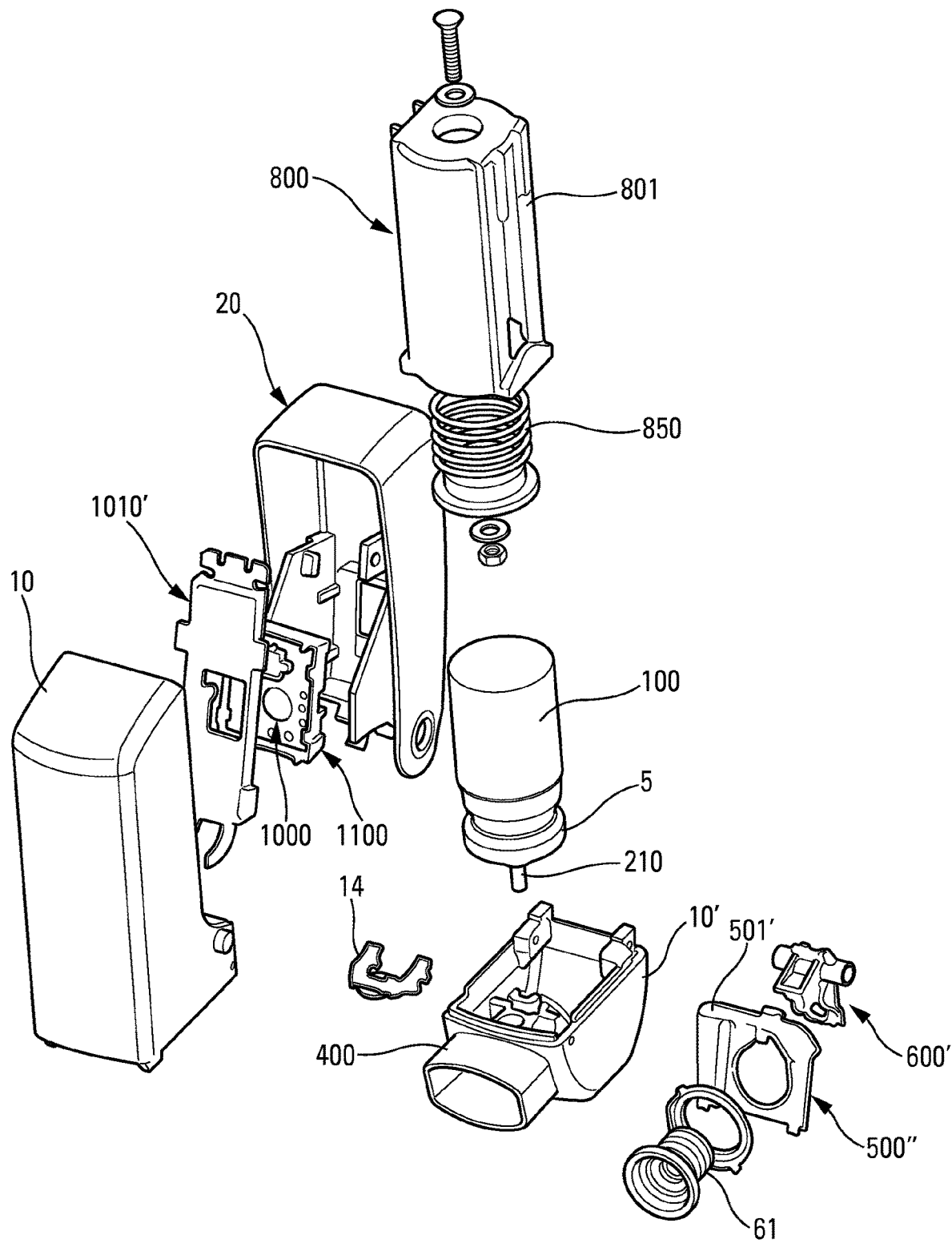
FIG. 10 is an exploded perspective view of the device in FIGS. 8 and 9.

During inhaling, the deformable membrane 61 deforms and/or contracts under the effect of the suction generated by inhaling, causing the trigger element 600 to move from its blocking position towards its release position. This then enables said blocking tabs 501 to deform, and thus enables said blocking ring 500 that forms the actuator element to move from its non-actuation position towards its actuation position. FIG. 1 shows a deformable membrane 61 made in the form of a pouch or a diaphragm. Naturally, other embodiments can also be envisaged, e.g. a bellows as shown in FIGS. 8 to 10.

The valve 200 is thus actuated only at the moment of inhaling, such that the dose of fluid is expelled out of the dispenser orifice simultaneously with inhaling. The dispensing of the dose is counted by the counter 1000, and information about dose taking, e.g. a timestamp and parameters of the inhalation flow, are transmitted by the transmitter means 1100.

When the user wishes to use the device, the user places the mouthpiece 400 in the mouth, and presses manually on the bottom of the reservoir 100, i.e. the top surface of said reservoir 100 in the position in FIG. 1. The reservoir 100 is then blocked and prevented from sliding in the body 10 by the blocking tabs 501 of the blocking ring 500, which blocking tabs bear against the shoulder 710 of the valve well 700. Optionally, the reservoir 100 may perform a short stroke before becoming blocked, this initial small stroke however being insufficient to actuate the metering valve 200.

When the user inhales through the mouthpiece 400, the deformable membrane 61 deforms, and this causes the trigger element 600 that is fastened to said deformable membrane 61 to slide. The movement of the trigger element 600 over the valve well 700 releases the tabs 501 of the blocking ring 500 radially. Under the effect of the axial force transmitted by the reservoir 100, generated by the user who is pressing on the bottom of said reservoir 100, the axial tabs 501 are able to deform radially outwards, and thus pass over said shoulder 710, so as to enable the reservoir 100 to slide towards its dispensing position, and the valve 200 thus to be actuated.

At the end of inhaling, the trigger element 600 is returned upwards by the springiness of the membrane 61.

When the user releases the pressure on the bottom of the reservoir 100, said reservoir returns towards the rest position under the effect of the return spring of the valve 200, and the valve member 210 of the metering valve simultaneously returns to the rest position, once again filling the valve chamber with a new dose of fluid. The device is thus ready for another utilization.

Figure 2:
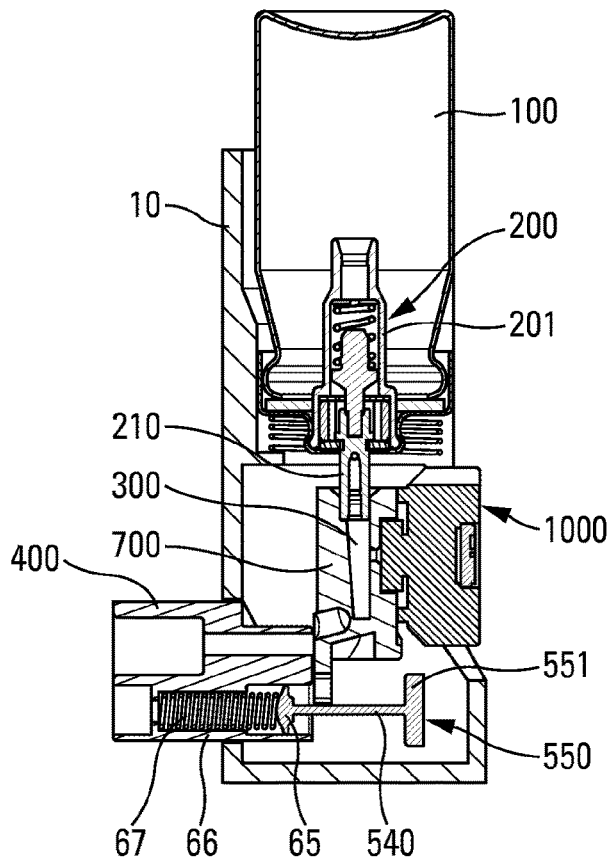
FIG. 2 is a diagrammatic section view of a fluid dispenser device, in another advantageous embodiment, in the rest position.
Figure 3:
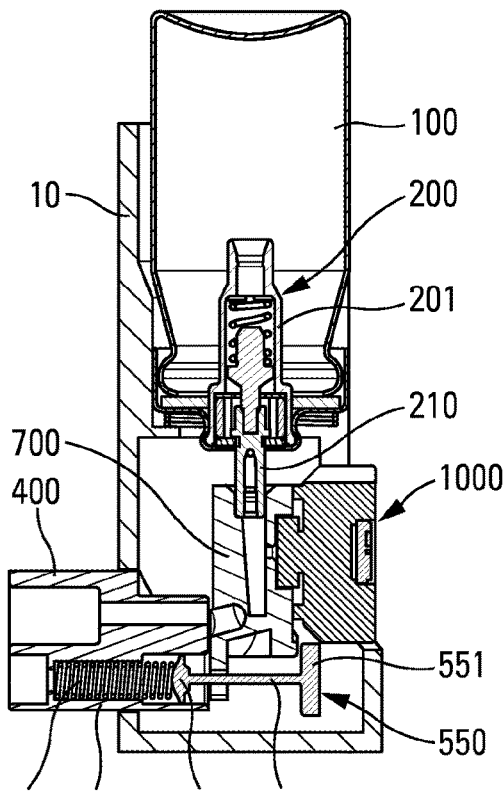
FIG. 3 is a view similar to the view in FIG. 2, when the user attempts to actuate the device without inhaling.
Figure 4:
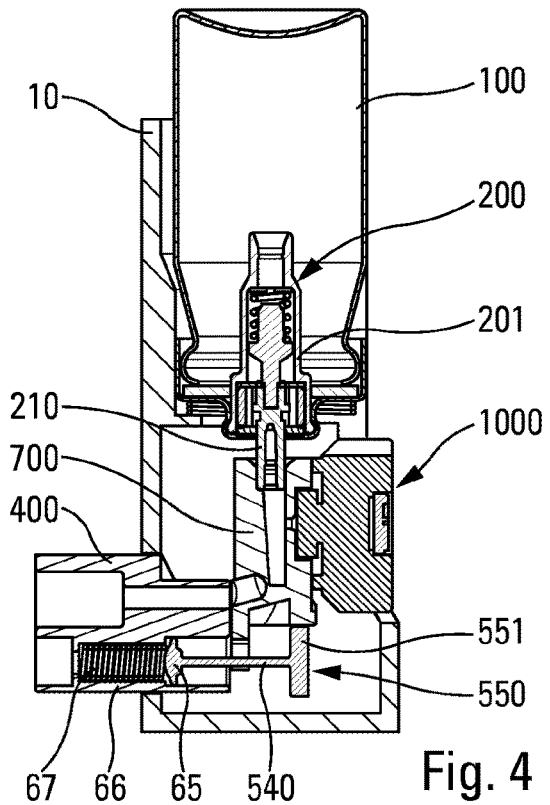
FIG. 4 is a view similar to the view in FIG. 3, when the user actuates the device while inhaling simultaneously.

FIGS. 2 to 4 show still another embodiment of the invention. In this embodiment, the actuator element is a locking element 550 that, in its non-actuation position, enables the valve member 210 of the metering valve 200 to move axially in the body 10, together with the reservoir 100, preventing said metering valve 200 from being actuated when said reservoir 100 is moved axially in the body 10 without inhaling. During inhaling, the locking element 550 is moved and/or deformed so that it prevents the valve member 210 from moving axially relative to the body 10. Thus, after inhaling, axial movement of the reservoir 100 causes the metering valve 200 to be actuated and a dose of fluid to be dispensed, synchronously with the inhaling.

The inhalation-sensitive member is made in the form of a piston 65 that slides in a chamber 66 between a rest position and an inhaling position. The chamber 66 is advantageously formed in the mouthpiece 400. Said piston 65 is connected to said locking element 550, advantageously via a rod 540. In particular, as can be seen in FIGS. 2 to 4, the locking element 550 may be formed at the end of said rod 540 remote from said piston 65, and comprises an axial projection 551. A spring 67, advantageously arranged in the chamber 66, is adapted to return said piston 65 towards its rest position when there is no longer any inhaling through the mouthpiece 400

In the non-actuation position, said projection is radially offset relative to the valve well 700, so that said valve well may move axially in the body 10, together with the valve member 210 of the metering valve 200 and the reservoir 100. Thus, in this non-actuation position, the valve member 210 does not move relative to the reservoir 100, and the metering valve 200 is thus not actuated.

When the user inhales through the mouthpiece 400, the piston 65 moves radially (relative to the movement axis A of the reservoir 100 in the body 10) in the chamber 66 under the effect of the suction created by inhaling. The projection 551 is thus moved radially also, and comes to be positioned below said valve well 700, thereby forming an abutment to the downward axial movement of said valve well. As a result, the pressure exerted by the user on the bottom of the reservoir 100 moves said reservoir axially downwards in the body, and the valve well 700 that is now axially stationary relative to the body 10, thus blocks the valve member 210 of the metering valve axially relative to the body 10, so that it is driven into the valve body, thereby causing the metering valve 200 to be actuated and a dose of fluid to be dispensed.

Naturally, in this embodiment in which the reservoir 100 is movable axially in the body 10 both in the actuation position and in the non-actuation position of the actuator element 550, the dose counter 1000 cannot measure the axial movement of the reservoir 100. In this circumstance, it is preferable to use sensors that detect the dispensing of the fluid, in particular in the valve well 700, or sensors that detect the movement of the valve member 210 of the metering valve 200 relative to the valve body 201.

FIGS. 5 to 7 show still another embodiment. In this embodiment, the trigger system that is triggered by inhaling is similar to the trigger system described above with reference to FIGS. 2 to 4, with a piston 65 that slides radially in a chamber 66 of the mouthpiece 400.

In this embodiment, the actuator element is once again made in the form of a blocking element 500' that, in the non-actuation position, prevents the reservoir 100 from moving axially in the body 10. During inhaling, the blocking element 500' is moved and/or deformed so that it no longer prevents the reservoir 100 from moving axially in the body 10. Thus, after inhaling, such axial movement of the reservoir 100 causes the metering valve 200 to be actuated and a dose of fluid to be dispensed, synchronously with the inhaling.

In particular, the blocking element 500' may be assembled on said rod 540 that is secured to the piston 65, and may include an axial extension 505 that, in the non-actuation position, extends axially in the body so as to co-operate with said reservoir 100 and block it axially. When the user inhales, the rod 540 moves radially towards the left (in the orientation in FIGS. 5 to 7), and this causes said axial extension 505 to deform, and thus to release the reservoir 100 to move axially. In the embodiment shown, the valve well 700 is mounted to move in the body 10, but it could also be stationary.

Advantageously, the bottom end 506 of said axial extension 505 is fastened radially and axially relative to the body 10. Thus, when the rod 540 moves radially, it pulls radially on said axial extension which deforms, e.g. bends or pivots, such that the top end is disengaged from the reservoir 100 and releases said reservoir so as to enable it to move axially. Naturally, the blocking element 500' could be of any other appropriate form. In particular, it is possible to envisage using a hinged toggle.

FIG. 7 shows a variant embodiment in which the rod 540 is accessible from the outside of the body 10 through an opening 19 of said body 10. This makes it possible, where necessary, to move the blocking element 500' manually, so as to be able to actuate the metering valve 200 even without inhaling, e.g. when the person that needs to receive the dose of fluid is incapable of inhaling sufficiently. This is thus a safety measure. It should be observed that this safety measure could also be adapted to the embodiment in FIGS. 2 to 4.

In the embodiment in FIGS. 8 to 10, an actuator member 800 is assembled on the top end of the reservoir 100, axially remote from said metering valve 200. The actuator member 800 comprises a hollow sleeve 801 that is arranged in the body 10 around the reservoir 100, with a spring 850 arranged between the bottom of the reservoir 100 and the closed top edge of said hollow sleeve 801. The hollow sleeve 801 is axially movable relative to said reservoir 100 between a rest position and a primed position. Thus, when the user wishes to move the reservoir 100 axially in the body 10, so as to actuate the metering valve 200, the user presses on said actuator member 800. This moves said hollow sleeve 801 axially towards its primed position and thus compresses said spring 850, which thus transmits an axial force F to said reservoir 100 which is substantially the same on each actuation. While the user continues to press on said actuator member 800, said spring 850 is compressed and drives said reservoir 100 axially towards its actuated position.

In the variant in FIGS. 8 to 10, a laterally-actuated pusher 20 is mounted to pivot on the body 10. When moved from its rest position shown in FIG. 8, to its working position shown in FIG. 9, the pusher comes to move said actuator member 800 axially so as to compress the spring 850. In particular, this can be done by means of a cam on the pusher 20, that co-operates with a complementary profile on the actuator member 800. While the user continues to press on said pusher, said spring 850 is compressed and drives said reservoir 100 axially towards its actuated position. Advantageously, said pusher 20 includes a drive member that drives said pusher 20 towards its rest position. Thus, when the user relaxes the pressure on the pusher 20, said pusher returns automatically into its rest position. This makes it possible to avoid the risk, after actuating the metering valve 200, of said metering valve remaining in its actuated position, which could cause the valve chamber to fill with air and the following dose to be incomplete, or it could cause the valve to leak. This is one of the problems that currently exists with devices that are currently on the market.

Naturally, the pusher 20 is not necessary, nor is the actuator member 800, since the user is able to press directly on the bottom of the reservoir, as in the above embodiments.

Actuating the valve 200 and expelling a dose of fluid are thus possible only when the user inhales and simultaneously presses axially on the reservoir 100 so as to actuate the valve 200. As described above, it is possible to press axially on the reservoir 100 by means of the actuator member 800 that compresses the spring 850. In a variant, the user could press directly on the bottom of the reservoir 100. In the variant in FIGS. 8 to 10, it is the pusher 20 that generates the axial pressure, also via the actuator member 800 in the embodiment shown. Finally, it is also possible to use an automatic actuator system that would apply the axial pressure on the reservoir 100 independently of the user.

In the embodiment in FIGS. 8 to 10, the actuator element is a blocking element 500" that, in the non-actuation position, prevents the reservoir 100 from moving axially in the body 10.

The blocking element 500" is advantageously mounted to pivot about an axis B on the body 10, or on the body portion 10', between a blocking position and an actuation position. In the embodiment shown, said axis B passes via a bottom edge of said blocking element 500".

The blocking element 500" includes at least one, preferably two, blocking extensions 501', that co-operate in the blocking position with the reservoir 100 (advantageously with the crimping cap 5).

The blocking element 500" is held in its blocking position by a trigger element 600'. The trigger element 600 is mounted to pivot about an axis C on the body 10, on the body portion 10', or on the pusher 20, between a locking position in which it blocks said blocking element 500" in its blocking position, and a release position in which it no longer blocks said blocking element 500". In the embodiment shown, said axis C passes approximately in the middle of said element of said trigger element 600'. Advantageously, the axes B and C are parallel.

The blocking element 500" and the trigger element 600' co-operate with each other to define a latch. In particular, said trigger element 600' includes a locking shoulder that, in the locking position, co-operates with a projection of the blocking element 500", preventing said blocking element 500" from pivoting out of its blocking position. Thus, when said trigger element 600' is in its locking position, it prevents the blocking element 500" from moving towards its actuation position, thereby preventing the reservoir 100 from moving axially and the metering valve 200 from thus being actuated.

By means of this latch force system, the force necessary to cause the trigger element 600' to pivot is very small and may be generated by the deformable membrane 61, that makes it possible to transform the suction generated by inhaling into unlocking force.

Advantageously, the bottom body portion 10' includes an opening 13 that is connected to the inside of the body 10. The opening 13 is closed at rest and at the start of inhaling by a check valve 14, so that the inhalation flow due to inhaling initially passes mainly to the trigger system, in this embodiment the deformable air chamber 60. This makes it possible to optimize such triggering by inhaling. When the blocking element 500" is moved towards its actuation position under the effect of inhaling, and thus when the user can actuate the metering valve 200 so as to dispense a dose of fluid, said blocking element 500" moves said check valve 14 towards an open position. When said openings 13 are thus open, air is drawn in, thereby making it possible to increase the inhalation flow. This optimizes synchronization between the user inhaling and dispensing the dose, and also promotes good dispensing of the dose into the user's lungs.

Advantageously, the trigger element 600' may be accessible from the outside of the body 10 and/or of the bottom body portion 10'. This makes it possible, if necessary, to move the trigger element 600' manually, so as to be able to actuate the metering valve 200 even without inhaling, e.g. when the person that needs to receive the dose of fluid is incapable of inhaling sufficiently. This is thus a safety measure.

In the embodiment shown in FIGS. 8 to 10, the inhalation-sensitive member is made in the form of a deformable air chamber 60. Advantageously, the air chamber comprises a deformable membrane 61 that is connected firstly to said bottom body portion 10' and secondly to said trigger element 600'. Advantageously, as can be seen in the figures, the membrane 61 is in the form of a bellows and forms a substantially airtight chamber. Other forms are possible, in particular a mere pouch or diaphragm. A lug may fasten said membrane 61 to an orifice of said trigger element 600'.

During inhaling, the deformable membrane 61 deforms and/or contracts under the effect of the suction generated by inhaling, causing the trigger element 600' to move from its locking position towards its release position. This makes it possible to open the latch defined between the blocking element 500" and the trigger element 600', and thus to move said blocking element 500" from its blocking position towards its actuation position.

The valve 200 is thus actuated only at the moment of inhaling, such that the dose of fluid is expelled out of the dispenser orifice simultaneously with inhaling.

Advantageously, the actuator member 800 includes a blocking tab (not shown), that is able to co-operate in its rest position with said trigger element 600', so as to prevent said trigger element from moving towards its release position. Thus, when the user inhales without having pressed axially on the reservoir 100, the latch is not unblocked, since the trigger element 600' cannot pivot. Since the air chamber 60 is substantially airtight, and the check valve 14 is closed in the opening 13, the user very quickly realizes that it is not possible to inhale correctly through the mouthpiece 400, which reminds the user that it is necessary to exert axial pressure on the reservoir 100 first before inhaling. When the user presses on the actuator member 800, the sleeve 801 is moved axially relative to the reservoir 100, which is itself blocked by the blocking element 500, and this compresses the spring 850. Inhaling thus causes the trigger element 600 to pivot, and thus causes the device to be actuated, as explained above.

When the user wishes to use the device, the user places the mouthpiece 400 in the mouth, and exerts axial pressure manually on the bottom of the reservoir 100, i.e. the top surface of said reservoir 100 in the position in the figures. The reservoir 100 is blocked and prevented from sliding axially in the body 10 by the blocking extensions 501 of the blocking element 500". Simultaneously, the trigger element 600' is no longer blocked as a result of the axial movement of the actuator member 800.

When the user inhales through the mouthpiece 400, the deformable membrane 61 deforms, and this causes the trigger element 600' that is fastened to said deformable membrane 61 to pivot. The movement of the trigger element 600' releases the latch formed between the trigger element 600' and the blocking element 500". Under the effect of the axial force transmitted by the reservoir 100, generated by pressing axially on the bottom of said reservoir 100, the blocking element 500" pivots enabling the reservoir 100 to slide axially in the body 10 towards its dispensing position, and the valve 200 thus to be actuated. Simultaneously, the blocking element 500" opens the check valve 14.

At the end of inhaling, when the user releases the pressure on the bottom of the reservoir 100, said reservoir rises axially in the body towards its rest position under the effect of the return spring of the valve 200, and the valve member 210 of the metering valve simultaneously returns to the rest position, once again filling the valve chamber with a new dose of fluid. The trigger element 600' is returned into its initial position by the springiness of the membrane 61 and/or by the actuator member 800 that returns towards its rest position. The blocking element 500" returns into its blocking position, advantageously via a resilient element, such as a spring or an element made of elastomer (not shown).

The device is thus ready for another utilization.

In particular, the electronic dose counter 1000 may be assembled in the pusher 20. In particular, the counter 1000 may detect the movements of the reservoir 100, e.g. by means of a slider 1010' that is moved by the reservoir 100 or by the blocking element 500", when they arrive in the dispensing position. In a variant, the counter 1000 could be connected to a sensor, in particular a membrane sensor, that detects the dose of fluid being dispensed, e.g. in the valve well 700. The electronic counter 1000 may be actuated in other ways, e.g. by detecting the movement of the valve member 210 of the metering valve relative to the valve body 201.

Preferably, the device also includes signal-transmitter means 1100 for communicating, in particular communicating remotely, information relating to the actuations of the device. In particular, the body 10 and/or the pusher 20 may include a signal-transmitter module, for communicating remotely with any base. Appropriate power supply means are advantageously provided.

In the embodiment shown in FIGS. 8 to 10, the electronic modules 1000, 1100 and the associated slider 1010' are positioned in the pusher 20, movable relative to the body 10. But, in a variant, it is possible to envisage modules that are stationary relative to the body 10.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to various advantageous embodiments and variants, but naturally any useful modification could be applied thereto by the person skilled in the art, without going beyond the ambit of the present invention, as defined by the accompanying claims.

The invention claimed is:

1. An inhalation-synchronized fluid dispenser device comprising a body provided with a mouthpiece, a fluid reservoir containing a fluid and a propellant gas mounted to slide axially in said body, a metering valve including a valve member assembled on said reservoir for selectively dispensing the fluid, said device further comprises:

an actuator element that is movable and/or deformable between a non-actuation position in which said metering valve (200) cannot be actuated, and an actuation position in which said metering valve can be actuated;

an inhalation-controlled trigger system including an inhalation-sensitive member that is deformable and/or movable under the effect of inhaling, said inhalation-sensitive member, when deformed and/or moved, moving and/or deforming said actuator element from the non-actuation position towards the actuation position;

an electronic dose counter; and signal-transmitter means for communicating information relating to actuations of the device; and wherein an actuator member is assembled on the reservoir on the end that is axially remote from said metering valve, said actuator member comprising a hollow sleeve that is axially movable relative to said reservoir between a rest position and a primed position, a spring arranged between a bottom of the reservoir and a closed top edge of said hollow sleeve, such that when the user presses manually on said actuator member so as to move the actuator member towards the primed position, said spring is compressed, so as to transmit an axial force to said reservoir.

2. A device according to claim 1, wherein a laterally-actuated pusher is mounted to pivot on the body between a rest position, and a working position in which the laterally-actuated pusher axially moves said actuator member into the primed position.

3. The device according to claim 1, wherein said signal-transmitter means is configured for communicating remotely the information relating to the actuations of the device.

4. An inhalation-synchronized fluid dispenser device comprising a body provided with a mouthpiece, a fluid reservoir containing a fluid and a propellant gas mounted to slide axially in said body, a metering valve including a valve member assembled on said reservoir for selectively dispensing the fluid, said device further comprises:

an actuator element that is movable and/or deformable between a non-actuation position in which said metering valve (200) cannot be actuated, and an actuation position in which said metering valve can be actuated;

an inhalation-controlled trigger system including an inhalation-sensitive member that is deformable and/or movable under the effect of inhaling, said inhalation-sensitive member, when deformed and/or moved, moving and/or deforming said actuator element from the non-actuation position towards the actuation position;

an electronic dose counter; and signal-transmitter means for communicating information relating to the actuations of the device; and wherein said body includes an opening that connects the mouthpiece to the inside of the body, said opening being closed at the start of inhaling by a check valve, such that the inhalation flow due to inhaling initially passes mainly to the trigger system.

5. A device according to claim 4, wherein said check valve is opened when said actuator moves towards the actuation position.

6. The device according to claim 4, wherein said signal-transmitter means is configured for communicating remotely the information relating to the actuations of the device.

7. An inhalation-synchronized fluid dispenser device comprising a body provided with a mouthpiece, a fluid reservoir containing a fluid and a propellant gas mounted to slide axially in said body, a metering valve including a valve member assembled on said reservoir for selectively dispensing the fluid, said device further comprises:

an actuator element that is movable and/or deformable between a non-actuation position in which said metering valve (200) cannot be actuated, and an actuation position in which said metering valve can be actuated;

an inhalation-controlled trigger system including an inhalation-sensitive member that is deformable and/or movable under the effect of inhaling, said inhalation-sensitive member, when it is deformed and/or moved, moving and/or deforming said actuator element from the non-actuation position towards the actuation position;

an electronic dose counter; and signal-transmitter means for communicating information relating to the actuations of the device; and wherein said actuator element is a blocking element that, in the non-actuation position, co-operates firstly with the body and secondly with the reservoir so as to prevent said reservoir from moving axially in the body; and wherein said blocking element comprises an axial extension having a bottom end that is fastened radially and axially relative to said body, and a top end that co-operates with said reservoir in the non-actuation position.

8. A device according to claim 7, wherein said inhalation-controlled trigger system includes a piston that slides in a chamber between a rest position and an inhaling position.

9. A device according to claim 8, wherein said blocking element is assembled on a rod (540) that is secured to the piston (65), so that during inhaling, said rod moves radially, deforming and/or moving said axial extension towards the actuation position.

10. The device according to claim 7, wherein said signal-transmitter means is configured for communicating remotely the information relating to the actuations of the device.

11. An inhalation-synchronized fluid dispenser device comprising a body provided with a mouthpiece, a fluid reservoir containing a fluid and a propellant gas mounted to slide axially in said body, a metering valve including a valve member assembled on said reservoir for selectively dispensing the fluid, said device further comprises:

an actuator element that is movable and/or deformable between a non-actuation position in which said metering valve (200) cannot be actuated, and an actuation position in which said metering valve can be actuated;

an inhalation-controlled trigger system including an inhalation-sensitive member that is deformable and/or movable under the effect of inhaling, said inhalation-sensitive member, when it is deformed and/or moved, moving and/or deforming said actuator element from the non-actuation position towards the actuation position;

an electronic dose counter; and signal-transmitter means for communicating information relating to the actuations of the device; and wherein said actuator element is a locking element that, in its non-actuation position, enables said valve member of the metering valve to move axially in the body, together with said reservoir, preventing said metering valve from being actuated when said reservoir is moved axially in the body without inhaling.

12. A device according to claim 11, wherein, during inhaling, said locking element is moved and/or deformed to prevent the valve member from moving axially relative to the body.

13. A device according to claim 12, wherein said inhalation-controlled trigger system includes a piston that slides in a chamber between a rest position and an inhaling position.

14. A device according to claim 13, wherein said locking element is secured to a rod that is secured to the piston, so that during inhaling, said rod moves radially, moving said locking element towards the actuation position in which the locking element prevents said valve member of the metering valve from moving axially when said reservoir is moved axially in the body.

15. The device according to claim 11, wherein said signal-transmitter means is configured for communicating remotely the information relating to the actuations of the device.

\* \* \* \* \*